United States Patent [19]

Williams

[11] Plant 5,222

[45] Apr. 24, 1984

[54] FLORIBUNDA ROSE PLANT—WILBLANK VARIETY

[75] Inventor: J. Benjamin Williams, Silver Springs, Md.

[73] Assignee: Conard-Pyle Company, West Grove, Pa.

[21] Appl. No.: 393,873

[22] Filed: Jun. 30, 1982

[51] Int. Cl.[3] ..... A01H 5/00

[52] U.S. Cl. ..... Plt./23

[58] Field of Search ..... Plt./8, 23

*Primary Examiner*—Robert E. Bagwill

*Attorney, Agent, or Firm*—Burns, Doane, Swecker and Mathis

[57] ABSTRACT

A new and distinct variety of Floribunda rose plant is provided having highly attractive double white flowers with a yellow center. The new variety resulted from the crossing of the Ma Perkins variety U.S. Plant Pat. No. 1,143) and an unnamed seedling resulting from the cross of the Charlie McCarthy variety (non-patented) and the Easter Morning variety (U.S. Plant Pat. No. 2,177). The new variety is a vigorous grower and can easily attain a height of twenty-four inches in a growing season. This new variety is particularly well suited for garden use, but also thrives in a greenhouse environment.

2 Drawing Figures

SUMMARY OF THE INVENTION

The object of the present invention is to provide a new variety of rose plant of the Floribunda Class which is distinguished from prior varieties by the following combination of characteristics:

(a) from the physical standpoint the plant with light green adult wood has a low sometimes irregular bushy growth habit, forms dark green shiny leaves, and forms double flowers which are white with a bright yellow center; and (b) from the biological standpoint the plant has vigorous and sometimes regular vegetation, exhibits copious and repeated florescence, exhibits the ability for its flowers to clean well, and exhibits the ability to grow well in either an outdoor or greenhouse environment.

The vigor of the new variety will enable it to easily attain a height of twenty-four inches in a growing season.

In view of these characteristics the new variety meets the needs of the horticultural industry and particularly is well-suited for garden use or for forcing in the greenhouse.

The new variety resulted from artificial pollination with the variety Ma Perkins (U.S. Plant Pat. No. 1,143) serving as the seed parent, and an unnamed seedling serving as the pollen parent which was formed by crossing the variety Charlie McCarthy (non-patented) and the variety Easter Morning (U.S. Plant Pat. No. 2,177).

The characteristics and properties of this new variety have been found to be transmissible by vegetative propagation through softwood cuttings, grafting and budding performed at West Grove, Pa.

The rose plant of the new variety has been named the Wilblank variety. Plants of the new variety presently are being marketed by the Conard-Pyle Co. of West Grove, Pa., under the Stardance trademark and are members of a family of floribunda rose plants which presently are being marketed by such company under the Miniflora trademark.

BRIEF DESCRIPTION OF THE PHOTOGRAPHS

The accompanying photographs show as nearly true as it is possible to make the same in color illustrations of this character, typical specimens of a plant and plant parts from two year old plants produced from softwood cuttings and growing in the open air during mid-June at West Grove, Pa.

In FIG.1 is shown a complete blossoming plant of the new variety wherein the yellow center of the white blossoms is clearly visible.

In FIG. 2 are shown various plant parts of the new variety. In the upper and left portions of the photograph are illustrated blossoms in various stages of opening. At the upper right portion of the photograph are shown a segment of a main branch and a segment of flowering stem (far right). In the lower left center of the photograph are shown three buds with the sepals in different stages of opening. In the lower right of the photograph is shown a cluster of buds prior to the opening of the sepals. In the lower left corner of the photograph is shown a leaf with seven leaflets. In the lower right center of the photograph is shown a leaf with five leaflets.

DETAILED DESCRIPTION

Figure 1:
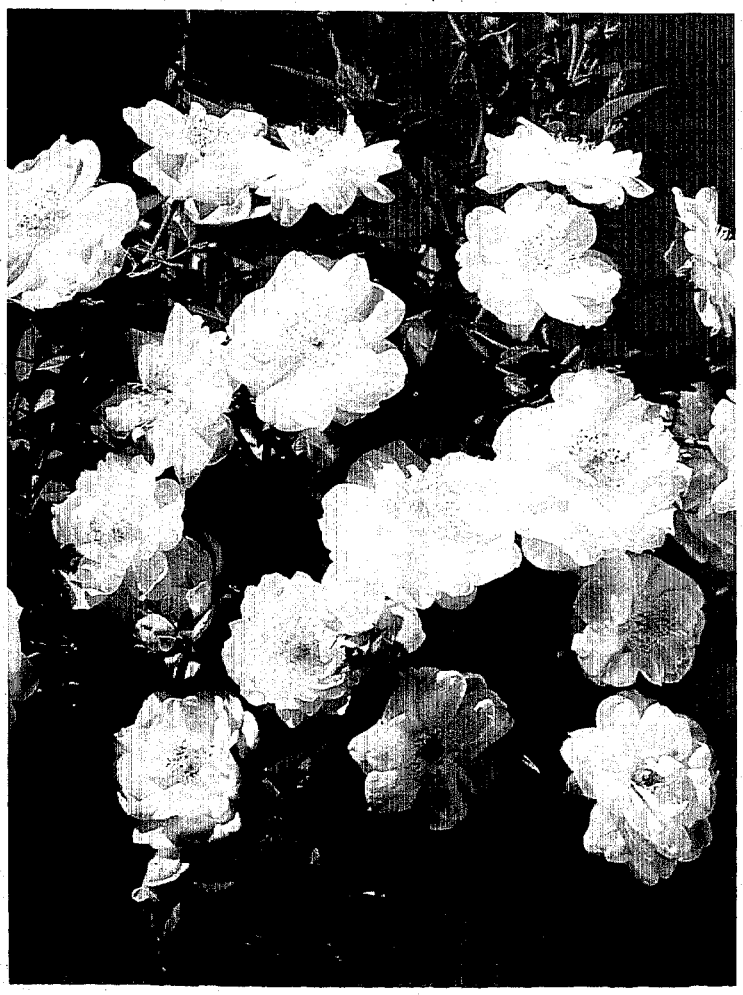
Figure 2:
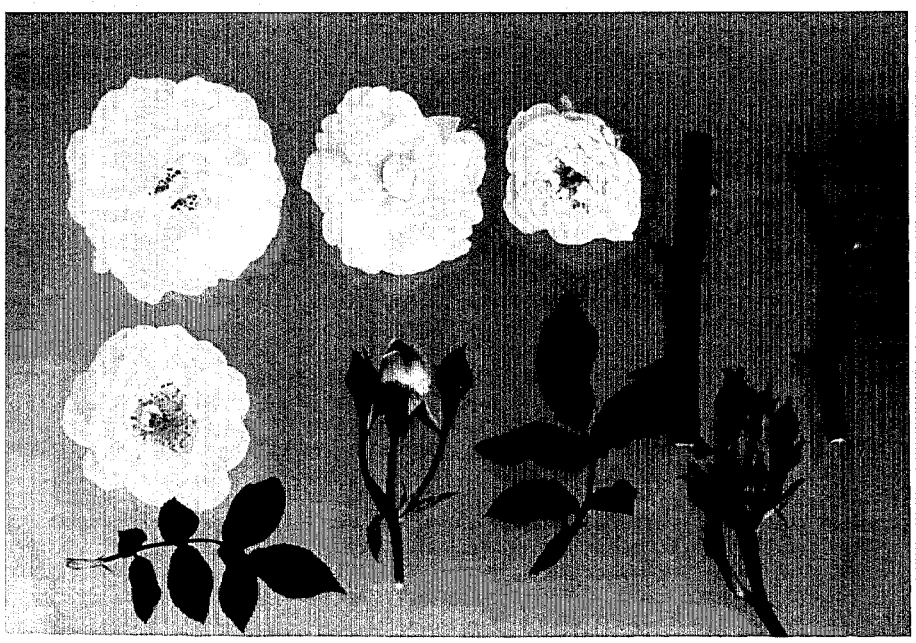

The plants described were grown outside during June at West Grove, Pa.

The chart utilized in the identification of the colors is that of The Royal Horticultural Society (R.H.S. Colour Chart).

Class: Floribunda.

Plant:

*Height.*—Approximately 60 to 80 cm. on average.

*Bearing.*—Bushy, semi-erect.

Branches:

*Color.*—Young stems: light bronzed-green, Yellow-Green Group 146B, reddish shading fades quickly as the stems mature. Mature wood: light green, Yellow-Green Group 144A.

*Thorns.*—Shape of upper edge: straight, occasionally convex. Shape of lower edge: vaguely concave. Size: medium. Quantity: sparse. Color: usually a straw color with a reddish tint on younger canes.

Foliage:

*Stipules.*—Narrow, linear, commonly approximately 2 to 2.5 cm. in length, serrated edge, recurving toward the cane.

*Petiole.*—Inner surface: narrow, grooved, tomentose, edge of grooves is lined with small red prickles, reddish green (young leaves), and light green (mature leaves). Outer surface: reddish (young leaves), light green lined with straw coloration (mature leaves), prickles are present.

*Leaflets.*—Number: often 5, usually 7, and occasionally 9. Shape: elliptical, rounded base with acute apex, approximately 1.8 to 3.1 (e.g. 2.5) cm. in length on average, and approximately 1.0 to 2.0 (e.g. 1.4) cm. in width on average. Teeth: regular and serrulate. General effect: abundant, fairly dense and shiny.

*Color.*—Young leaves: Upper surface: dark green, darker than Green Group 143A. Lower surface: Yellow-Green Group 146C. Mature leaves: Upper surface: Green Group 139A. Lower surface: light green, Green Group 137C.

Flowers:

*Number of flowers.*—Usually 3 to 4 flowers per stem, though up to 10 flowers per stem is not uncommon.

*Peduncle.*—Slightly curved, light green with very heavy reddish pubescence, approximately 3 to 4 cm. in length on average.

*Sepals.*—Inner surface: tomentose, light green with white edge, sometimes with a red tip.Outer surface: light green, Yellow-Green Group 143C, covered with red pricklets, which impart a reddish cast.

*Bud.*—Shape: broadly ovoid. Length: approximately 1 cm. on average at opening of the sepals. Size: medium for type. Color on opening: warmer than Orange-White Group 159D on the petal inside, and White Group 155B on the petal outside.

*Flower.*—Shape: somewhat flat with cup-shaped center, petal edges are irregular with usually one notch. Diameter: approximately 5.0 to 6.0 cm. on average. Color: when first opening the inner petal surface is Orange-White Group 159D and the outer petal surface is White Group 155B. When fully open the petals are pure white. Fragrance: light. Lasting quality: fully open blooms commonly last one or two days. Texture: soft. Petal shape: obovate, with claw which is often very elongated. Number of petals: approximately 60 to 70 on average. Stamens: approximately 70 on average, filaments are Yellow Group 11A and impart to the bloom a distinct yellow center. As the flower ages, the bright yellow coloration of the filaments fades and the anthers darken. Pistils: thin, bunched, pale green.

Development:

*Vegetation.*—Vigorous and often irregular.

*Flowering.*—Very abundant and repeats well.

*Capacity for bearing fruit.*—Poor.

*Resistance to frost.*—Average for type.

*Resistance to diseases.*—Average for type.

I claim:

1. A new and distinct variety of Floribunda rose plant, substantially as illustrated and described, wherein:

(a) from the physical standpoint the plant with light green adult wood has a low sometimes irregular bushy growth habit, forms dark green shiny leaves, and forms double flowers which are white with a bright yellow center; and (b) from the biological standpoint the plant has vigorous and sometimes regular vegetation, exhibits copious and repeated florescence, exhibits the ability of its flowers to clean well, and exhibits the ability to grow well in either an outdoor or greenhouse environment.

* * * * *